United States Patent [19]

Moore et al.

[11] Patent Number: 5,851,801
[45] Date of Patent: Dec. 22, 1998

[54] METHOD OF PREPARING POLYPEPTIDE BINDING COMPOSITIONS DERIVED FROM IMMUNOGLOBULIN VARIABLE REGIONS

[75] Inventors: Kevin W. Moore, San Bruno; Alejandro Zaffaroni, Atherton, both of Calif.

[73] Assignee: Schering Corporation, Kenilworth, N.J.

[21] Appl. No.: 460,892

[22] Filed: Jun. 5, 1995

Related U.S. Application Data

[63] Continuation of Ser. No. 394,923, Feb. 23, 1995, abandoned, which is a continuation of Ser. No. 210,540, Mar. 17, 1994, abandoned, which is a continuation of Ser. No. 61,760, May 13, 1993, abandoned, which is a continuation of Ser. No. 928,526, Aug. 11, 1992, abandoned, which is a continuation of Ser. No. 740,862, Jul. 31, 1991, abandoned, which is a continuation of Ser. No. 235,835, Aug. 18, 1988, abandoned, which is a continuation of Ser. No. 880,300, Jun. 30, 1986, abandoned, which is a continuation of Ser. No. 558,551, Dec. 15, 1983, Pat. No. 4,642,334, which is a continuation of Ser. No. 358,414, Mar. 15, 1982, abandoned.

[51] Int. Cl.$^6$ .......................... C12P 21/00; C12P 21/08; C12N 15/13
[52] U.S. Cl. ........................................ 435/69.6; 435/172.3
[58] Field of Search .............................. 514/2; 435/240.2, 435/69.1, 69.6, 172.1, 172.3; 530/387.1, 387.3

[56] References Cited

U.S. PATENT DOCUMENTS 4,036,945    7/1977    Haber et al. ............................ 424/1.49

FOREIGN PATENT DOCUMENTS

A 0 035 265    9/1981    European Pat. Off. .

OTHER PUBLICATIONS

Early et al., "An Immunoglobulin heavy chain variable region gene is generated from three segments of DNA:Vh, D and Jh". Cell, vol. 19, pp. 981–992, Apr. 1980.
Amster et al., "Synthesis of part of a mouse immunoglobulin light chain in a bacterial clone", Nucleic Acids Res., vol. 8, No. 9, pp. 2055–2065, 1980.
Kooistra et al., "Magnetic resonance studies of the binding site interactions between 19F–labeled nitrophenyl haptens and specific mouse myleoma immunoglobulin MOPC–315", Biochemistry, vol. 17, No. 2, pp. 345–351, 1978.
Bodey et al., "Human cancer detection and immunotherapy with conjugated and non–conjugated nonoclonal antibodies", Anticancer Res., vol. 16, pp. 661–674, 1996.
Jain, R.K., "Vascular and interstitial barriers to delivery of therapeutic agents in tumors", Cancer Metastasis Rev., vol. 9, pp. 253–266. (Abstract only), 1990.
Baumgartner et al., "Immunotherapy of endotoxemia and septicemia", Immunobiology, vol. 187, pp. 464–477, Apr. 1993.
Givol, 1974, *Essays in Biochemistry* 10:73–104.
Gough, Aug., 1981, *TIBS* 203–205.
Early et al., 1981, *Genetic Engineering: Principles and Methods* 3:157–183.
Leder, 1982, *Scientific American* 246(5):72–83.
Gough et al., 1980, *Biochemistry* 19:2702–2710.
Adams et al., 1980, *Biochemistry* 19:2711–2719.
Inbar et al., *Proc. Nat. Acad. Sci. USA* 69(9):2659–2662.
Hochman et al., 1973, *Biochemistry* 12(6):1130–1135.
Sharon et al., 1976, *Biochemistry* 15(7):1591–1594.
Kooistra et al., 1978, *Biochemistry* 17(2):345–351.
Accolla et al., 1980, *Proc. Nat. Acad. Sci., USA* 77(1):563–566.
O'Sullivan et al., 1979, *Annals of Clinical Biochemistry* 16:221–240.
Miozzari et al., 1978, *J. Bacteriol.* 133(3):1457–1466.
Plückthun, 1991, *Bio/technology* 9:545–551.
Kakimoto et al., 1974, *The Journal of Immunology* 112(4):1373–1382.
Lin et al., 1978, *Proc. Natl. Acad. Sci. USA* 75(6):2649–2653.
Rosemblatt et al., 1978, *Biochemistry* 17:3877–3882.
Cunningham, *Understanding Immunology*, pp. 38–39.
Alberts, 1989, *Molecular biology of the cell*, pp. 1025–1026.
Francis et al., 1974, *Proc. Nat. Acad. Sci.*, 71:1123–1127.
Raso et al., 1980, *Journal of Immunology* 125(6):2610–2616.
Hales et al., 1980, *Methods in enzymology* 70:334–355.
O'Sullivan et al., 1981, *Methods in enzymology* 73:147–166.
Boss et al., 1984, *Nucleic Acids Research* 12:3791–3806.
Wood et al., 1985, *Nature* 314:446–448.
Cabilly et al., 1984, *Proc. Natl. Acad. Sci. USA* 81;3273–3277.
Kenton et al., 1984, *Proc. Natl. Acad. Sci. USA* 81:2955–2599.
Liu et al., 1984, *Proc. Natl. Acad. Sci. USA* 81:5369–5373.
Gherna et al., 1985, *American Type Culture Collection* Sixteenth edition, p. 243.
Gubler et al., 1986, *J. Immunol.* 136:2492–2497.
Saxena et al., 1970, *Biochemistry* 9:5015–5023.

*Primary Examiner*—David Guzo
*Attorney, Agent, or Firm*—Cynthia L. Foulke; Edwin P. Ching

[57] ABSTRACT

Proteinaceous binding compositions are prepared employing hybrid DNA technology, where the variable region polypeptides of immunoglobulins are substantially reproduced to provide relatively small protein molecules having binding specificity and lacking the undesirable aspects of the heavy regions of immunoglobulins. The compositions find a wide range of use, particularly for physiological purposes for diagnosis and therapy. The binding compositions may be modified by labeling with radioisotopes, fluorescers, and toxins for specific applications in diagnosis or therapy.

3 Claims, No Drawings

METHOD OF PREPARING POLYPEPTIDE BINDING COMPOSITIONS DERIVED FROM IMMUNOGLOBULIN VARIABLE REGIONS

This application is a continuation of application Ser. No. 08/394,923, filed Feb. 23, 1995, now abandoned, which is a continuation of application Ser. No. 08/210,540, filed Mar. 17, 1994, now abandoned, which is a continuation of application Ser. No. 08/061,760, filed May 13, 1993, now abandoned, which is a continuation of application Ser. No. 07/928,526, filed Aug. 11, 1992, now abandoned, which is a continuation of application Ser. No. 07/740,862, filed Jul. 31, 1991, now abandoned, which is a continuation of application Ser. No. 07/235,835, filed Aug. 18, 1988, now abandoned, which is a continuation of application Ser. No. 06/880,300, filed Jun. 30, 1986 abandoned, which is a continuation of application Ser. No. 06/558,551, filed Dec. 5, 1983, now U.S. Pat. No. 4,642,334, which is a continuation of application Ser. No. 06/358,414, filed Mar. 15, 1982, now abandoned.

BACKGROUND OF THE INVENTION

1. Field of the Invention

The mammalian immunological system is unique in its broad ability to produce protein compounds having extremely high specificity for a particular molecular structure. That is, the proteins or immunoglobulins which are produced have a conformation which is specifically able to complement a particular structure, so that binding occurs with high affinity. In this manner, the mammalian immune system is able to respond to invasions of foreign molecules, particularly proteins in surface membranes of microorganisms, and toxins, resulting in detoxification or destruction of the invader, without adverse effects on the host.

The primary immunoglobulin involved in the defensive mechanism is gamma-globulin (IgG). This immunoglobulin, which is a glycoprotein of about 150,000 daltons, has four chains, two heavy chains and two light chains. Each of the chains has a variable region and a constant region. The variable regions are concerned with the binding specificity of the immunoglobulin, while the constant regions have a number of other functions which do not directly relate to the antibody affinity.

In many situations it would be desirable to have molecules which are substantially smaller than the immunoglobulins, while still providing the specificity and affinity which the immunoglobulins afford. Smaller molecules can provide for shorter residence times in a mammalian host. In addition, where the immunoglobulin has to be bound to another molecule, it will be frequently desirable to minimize the size of the final product. Also there are many economies in being able to produce a smaller molecule which fulfills the function of a larger molecule.

There are situations where it will be desirable to be able to have a large number of molecules compactly held together. By having smaller molecules, a greater number can be brought together into a smaller space. Furthermore, where the binding molecule can be prepared by hybrid DNA technology, one has the opportunity to bind the binding portion of the molecule to a wide variety of other polypeptides, so that one can have the binding molecule covalently bonded at one or both ends to a polypeptide chain.

Where immunoglobulins are used in in vivo diagnosis or therapy, antisera from an allogenic host or from a monoclonal antibody may be immunogenic. Furthermore, when conjugates of other molecules to the antibody are employed, the resulting conjugate may become immunogenic and elicit host antibodies against the constant region of the immunoglobulin or against any other part of the molecule.

It is therefore important that methods be developed which permit the preparation of homogeneous compositions having high specificity for a particular ligand, while avoiding the shortcomings of complete immunoglobulins, and providing the many advantages of lower molecular weight.

2. Description of the Prior Art

Discussions concerning variable regions of heavy and light chains of immunoglobulins may be found in Sharon and Givol, Biochem. (1976) 15:1591–1594; Rosemblatt and Haber, Biochem. (1978) 17:3877–3882; and Early and Hood, Genetic Engineering (1981) 3:157–188. Synthesis of part of a mouse immunoglobulin light chain in a bacterial clone is described by Amster et al., Nucleic Acids Res. (1980) 8:2055–2065. See also the references cited throughout the specification concerning particular methodologies and compositions.

SUMMARY OF THE INVENTION

Novel protein complexes are provided by producing homogeneous compositions defining the variable regions of the light and heavy chains of an immunoglobulin, which individually or together form a specific binding complex to a predetermined haptenic or determinant site. Employing hybrid DNA technology, cDNA is tailored to remove nucleotides extraneous to the variable regions of the light and heavy chains. The resulting tailored ds cDNA is inserted into an appropriate expression vector which is then introduced into a host for transcription and translation. The resulting truncated light and heavy chains define at least a major portion of the variable regions and are combined to form a complex capable of specifically binding to a predetermined haptenic site with high affinity.

DESCRIPTION OF THE SPECIFIC EMBODIMENTS

The subject invention concerns a hybrid DNA strategy for the preparation of specific binding polypeptides, normally comprised of two different polypeptide chains, which together assume a conformation having high binding affinity to a predetermined ligand or haptenic site thereof. The polypeptide chains form binding sites which specifically bind to a predetermined ligand to form a complex having strong binding between the ligand and the binding site. The binding constant or avidity will generally be greater than $10^5$, more usually greater than $10^6$, and preferably greater than $10^8$. The haptenic binding site or determinant binding site of the polypeptide chain may be associated with a hapten or antigen.

One or both of the different polypeptide chains derived from the variable region of the light and heavy chains of an immunoglobulin may be used to provide specific binding to a ligand. For the most part each of the polypeptide chains of the light and heavy variable regions would be employed together for binding to the ligand. In describing this invention, it will be understood that while the two different chains are indicated as forming a complex, either of the chains could be used individually, where feasible due to sufficient binding affinity of the particular chain to the reciprocal ligand.

The two polypeptide chains which, individually or together, provide the compositions of this invention will form a receptor site, analogous to the binding site of an immunoglobulin. The composition will be referred to as an rFv with the individual chains referred to as L-rFv or H-rFv. The L- and H- designations will normally mean light and heavy respectively, but in some instances the two chains may be the same and derived from either the light or heavy chain sequences. The polypeptide chains of the rFv will generally have fewer than 125 amino acids, more usually fewer than about 120 amino acids, while normally having greater than 60 amino acids, usually greater than about 95 amino acids, more usually greater than about 100 amino acids. Desirably, the H-rFv will be from about 110 to 125 amino acids while the L-rFv will be from about 95 to 115 amino acids.

The amino acid compositions will vary widely, depending upon the particular idiotype involved. Usually there will be at least two cysteines separated by from about 60 to 75 amino acids and joined by a disulfide bond to form cystine. The two chains will normally be substantial copies of idiotypes of the variable regions of the light and heavy chains of immunoglobulins, but in some situations it may be sufficient to have combinations of either the light or the heavy variable region chains.

In many instances, it will be desirable to have one or both of the rFv chains labeled or bound to a support. Various labels may be employed, such as radioisotopes, fluorescers, or toxins. In other situations, one or both of the chains may be bound to an inert physiologically acceptable support, such as synthetic organic polymers, polysaccharides, naturally occurring proteins, or other non-immunogenic substances.

In some situations, it may be desirable to provide for covalent crosslinking of the two chains, which could involve providing for cysteine residues at the carboxyl termini. The chains will normally be prepared free of the constant regions, including or being free of all or a portion of the J region. The D region will normally be included in the transcript of the H-rFv.

For the most part only a relatively small percent of the total amino acids will vary from idiotype to idiotype in the rFv. Therefore, there will be areas providing a relatively constant framework and areas that will vary, namely, the hypervariable regions.

The C-terminus region of the rFv will have a greater variety of sequences than the N-terminus and, based on the present strategy, can be further modified to permit variation from the naturally occurring heavy and light chains. A synthetic oligonucleotide can be employed to vary one or more amino acids in a hypervariable region.

The preparation of the rFv employing hybrid DNA technology will now be described in greater detail.

The preparation of the rFv will be divided into three parts: (1) isolation of appropriate DNA sequences; (2) introduction of the DNA sequences coding for the members of the rFv into an appropriate expression vector; and (3) expression and isolation of the mimetic variable regions of the light (L-rFv) and heavy (H-rFv) chains to provide the rFv.

I. Isolation of appropriate DNA Sequences.

In preparing the DNA sequences, a source of the genes encoding the variable region will be required. The variable regions may be derived from IgA, IgD, IgE, IgG or IgM, most commonly, from IgM and IgG. This can be achieved by immunizing an appropriate vertebrate, normally a domestic animal, and most conveniently a mouse. The immunization may be carried out conventionally with one or more repeated injections of the immunogen into the host mammal, normally at two to three week intervals. Usually three days after the last challenge, the spleen is removed and dissociated into single cells to be used for cell fusion to provide hybridomas.

The immunogen will be the antigen of interest, or where a hapten, an antigenic conjugate of the hapten to an antigen.

In order to prepare the hybridomas, the spleen cells are fused under conventional conditions employing a fusing agent, e.g. PEG6000, to a variety of inter- or intra-species myeloma cells, particularly mouse cells such as SP-2/0, NS-1, etc. and then suspended in HAT selective media. The surviving cells are then grown in microtiter wells and immunologically assayed for production of antibodies to the determinant site(s) of interest.

Assays for antibodies are well known in the art and may employ a variety of labeled antigens or haptens, where the labels are conveniently radioisotopes, fluorescers, enzymes, or the like. Other techniques may also be employed, such as sandwich techniques involving two antibodies, one bound to a support and the other being labeled. The cells from microtiter wells scored as positive are cloned either by limiting dilution or cloning in soft agar. The resulting cloned cell lines are then propagated in an appropriate nutrient medium and, if necessary, may be stored frozen in liquid nitrogen.

After selection of a particular cell line providing a monoclonal antibody of interest, the cells are expanded. Conveniently, the cells may be grown to a density of about $1 \times 10^6$ cells/ml in a 1 L culture. The cells are then harvested by centrifugation and lysed.

In order to obtain the desired DNA sequence, one can look to either the gene expressing the variable region or the messenger RNA, which expresses the variable region. The difficulty with employing genomic DNA is in juxtaposing the sequences coding for the variable region, where the sequences are separated by introns. One must isolate the DNA fragment(s) containing the proper exons, excise the introns and then splice the exons in the proper order and orientation. For the most part, this will be difficult, so that the alternative technique employing the messenger RNA will be the method of choice.

Where the messenger RNA is to be employed, the cells will be lysed under RNase inhibiting conditions. The messenger RNA has the advantage that the mature messenger is free of introns, so that the sequence is continuous for the entire variable region. Difficulties with messenger RNA have been encountered, due to incomplete reverse transcription but these difficulties can be minimized. The first step is to isolate the messenger RNA. Conveniently, messenger RNA can be separated from other RNA because of its polyadenylation, employing an oligo-(dT) cellulose column. The mixture of messenger RNAs will be obtained free of other RNA. The presence of messenger RNAs coding for the heavy and light chain polypeptides of the immunoglobulins may then be assayed by hybridization with DNA single strands of the appropriate genes. Conveniently, the sequences coding for the constant portion of the light and heavy chains may be used as probes, which sequences may be obtained from available sources (see, for example, Early and Hood, Genetic Engineering, Setlow and Hollaender eds. Vol. 3, Plenum Publishing Corp., New York (1981), pages 157–188.)

Whether the messenger RNA codes for the correct immunoglobulin may be determined by in vitro translation employing a rabbit reticulocyte cell-free extract (Pelham and Jackson, Eurp. J. Biochem. (1976) 66:247–256). The resulting translation product may then be isolated by employing antibodies specific for one or more of the regions of the chain of interest, for example, using rabbit anti(mouse IgG) where the chains are derived from mouse immunoglobulin.

The immunoprecipitate may be further analyzed by polyacrylamide gel electrophoresis, and the presence of complexes determined by using radiotagged receptors for antigen-antibody complexes, such as *S. aureus* protein A, Rf factor, or the like. In addition, RNA blot hybridization can be employed to further insure that the correct messenger RNA is present.

The crude mixture of mRNA sequences containing the desired mRNA sequences will be treated as follows. In order to enhance the probability that full length cDNA is obtained, the method of Okayama and Berg, Mol. Cell. Biol. (1982) may be employed. Alternatively, the methods described by Efstradiadis and Villa-Komaroff (1979) in Genetic Engineering: Principles and Methods 1, Setlow and Hollaender, eds., New York, Plenum Press, pages 15–36, or Steinmetz et al. (1981) Cell 24:125–134, may be employed. The first strand of cDNA is prepared employing a virus reverse transcriptase in the presence of primer. A second strand may then be prepared employing reverse transcriptase, the Klenow fragment of DNA polymerase I or T4 polymerase. If necessary, the resulting ds cDNA may then be treated with a single-strand-specific nuclease, such as S1 nuclease for removal of single stranded portions to result in ds cDNA, which may then be cloned.

II. Preparation of Genes Coding For L-rFv and H-rFv and Introduction into an Expression Vector For Amplification.

A wide variety of vectors may be employed for amplification or expression of the ds cDNA to produce the light and heavy chains of the immunoglobulin. A vector having an appropriate restriction site is digested with the appropriate endonuclease. The ds cDNA obtained from the reverse transcription of the mRNA may be modified by ligating linkers, treatment with terminal transferase or other techniques to provide staggered (complementary) or blunt ended termini. The vectors may have one, two or more markers for selection of transformants. Desirably, the vector will have a unique restriction site in one of multiple markers, so that the transformants may be selected by the expression of one marker and the absence of expression of the other marker. Various markers may be employed, such as biocide resistance, complementation of an auxotroph, viral immunity, or the like.

After transforming an appropriate host with the ds cDNA prepared from the mRNA, e.g. *E. coli, B. subtilis, S. cerevisiae*, etc., in accordance with conventional ways, the transformants are plated and selected in accordance with the particular markers. The resulting colonies are screened, by restriction electrophoretic pattern, hybridization to a labeled probe or by any other conventional means. See, for example, Hanahan and Meselson (1980), Gene 10:63–67. One procedure employs colony hybridization, where the transformants are grown on a solid medium to produce colonies. Cells from the colonies are transferred to a nitrocellulose replica filter, the transferred cells incubated for further growth, lysed, dried and baked. The replica filter is then hybridized with appropriate radioisotope labeled probes. Conveniently, there are readily available probes for the determinant sites present in the constant regions of a variety of mammalian immunoglobulins. The colonies may be probed based on the nature of the particular immunoglobulin, as well as the different determinant sites, which may be present with the particular immunoglobulin.

The host colonies, usually bacterial, which have DNA which hybridizes to either the light or heavy chain probes are picked and then grown in culture under selective pressure. In order to maintain selective pressure, it is desirable that the vector which is employed have biocidal, particularly antibiotic, resistance. After sufficient time for expansion of the host, the host cells are harvested, conveniently by centrifugation. The hybrid plasmid DNA may then be isolated by known procedures. (Gunsalus et al., J. Bacteriol. (1979) 140:106–133).

The isolated plasmid DNA is then characterized by restriction enzyme digestion and DNA sequence analysis. These analyses insure that the isolated cDNA clones completely encode the variable region and, optionally, the leader sequences for the light or heavy chain of the desired immunoglobulin. Furthermore, by having a restriction map of the variable regions and leader sequences, as well as the flanking sequences, one can determine the appropriate restriction sites for excising a DNA fragment which will allow for appropriate modification of the DNA sequence for insertion into a vector and expression of the polypeptide of interest. Where no unique restriction site is available at an appropriate position in the flanking regions, partial digestion may be employed, with selection of fragments having the variable region and, optionally, the leader sequence intact. Where the 5' and 3' flanking regions are too extended, these can be chewed back using Bal 31 to varying degrees by varying the period of digestion.

Furthermore, by knowing the DNA sequence of the coding strand in the region of the C-terminus of the heavy and light chain variable regions, a stop codon may be introduced at the C-terminus by the following procedure of in vitro mutagenesis. The cDNA is restricted with the appropriate enzyme(s) to provide a variable region coding segment with additional 5' and 3' flanking sequences. This segment is purified, for example, by gel electrophoresis, gradient density centrifugation, etc. After isolating the desired segment, the two strands of the segment are dissociated, conveniently by boiling. Alternatively, the undesired strand of the intact cDNA-plasmid clone may be nicked and digested.

A synthetic, single-stranded DNA oligomer is prepared, conveniently by synthesis, which will have at least about 12 nucleotides, more usually about 15 nucleotides, and will generally have fewer than about 50 nucleotides, usually fewer than 30 nucleotides, since a more extended oligomer is not required.

Where heteroduplexing is involved, the non-complementary nucleotides will usually be flanked by at least about three, more usually at least about six nucleotides complementary to the hybridized strand. The heteroduplexing oligonucleotide will be complementary to the sequence at or about a significant juncture i.e. between the leader sequence and the variable region or the variable region and the constant region. The synthetic DNA oligomer will be complementary to the coding ("sense") strand of the variable-region sequence, but altered to encode a termination codon at the C-terminus of the variable region. That is, the oligomer will be complementary to the coding strand except at or about the amino acid which is involved at the juncture of the variable region and the D-, J- or C-regions of the light and heavy chains, particularly at or intermediate the D- or J-regions or intermediate the J-region, or at the J-region and C-region juncture. It is intended that there will be some variation in the polypeptides which are prepared, so far as extending beyond the variable domains or not including all of the amino acids at the C-terminus of the variable region.

An excess amount of the oligomer is combined with the denatured strands of the restriction fragment under sufficiently stringent hybridization conditions. Thus, the oligomer specifically heteroduplexes to the complementary portions of the coding strand, while providing one or more stop and/or nonsense codons to insure the termination of expression at the desired amino acid at the C-terminus.

After sufficient time for hybridization at the desired level of stringency, sufficient amounts of the four deoxynucleotides are added in conjunction with the Klenow fragment of DNA polymerase I. A strand complementary to the coding sequence of the variable-region and any 5'-flanking sequence is synthesized by enzymatic elongation of the primer resulting in a sequence complementary to the strand to which the oligonucleotide is bound. The single-stranded DNA sequence on the coding strand located 3' to the region hybridized to the synthetic oligonucleotide is degraded by the 3'-5' exonuclease activity of the DNA polymerase. In this manner, ds cDNA is obtained which specifically codes for the variable-region and upstream flanking regions associated with the light and heavy chains. Each of the heavy and light chains is encoded to terminate expression at a predetermined codon in the V, D or J region.

The resulting heteroduplexed blunt-ended ds cDNA fragments are then employed for preparation of homoduplexed ds cDNA coding for the light and heavy variable regions with the stop codons at the desired sites. Conveniently, the blunt ended fragments are modified as described previously, e.g. joined to linkers which code for restriction sites which are absent in the variable region sequences, or may be tailed e.g. polyG or polyC, or used directly for insertion. With restriction site linkers, after insertion of the fragment into an appropriate vector having complementary termini, the fragment can be recovered by restriction at the linker sites. The linkers are joined to the coding sequences with an appropriate ligase, e.g. T4 ligase, the resulting fragment restricted to provide cohesive ends, and the product annealed to the complementary ends of a vector.

At this stage, the vector which is employed provides for amplification and convenient isolation of transformants having the variable region coding sequence insert. Numerous vectors for amplification in bacteria or other hosts exist such as pBR322, pSC101, pRK290, 2 $\mu$-plasmid, etc. The hybrid plasmid containing the mismatched sequences will replicate in the host to generate two different plasmid molecules, one with the original sequence and one with the "tailored" or "site mutated" sequence derived from the synthetic oligonucleotide. Therefore, each transformant colony is grown in small (approximately 2 ml) culture for plasmid isolation.

The transformants are grown, the plasmid DNA isolated in accordance with known procedures, and used for a. second cycle of transformation to provide individual clones replicating the tailored sequence. The clones may be screened by filter blot hybridization, probing with a labeled synthetic oligonucleotide which. will include the synthetic oligonucleotide employed in tailoring the variable region sequence, or other convenient technique. Thus, plasmids are obtained having ds cDNA flanked by appropriate restriction sites and having a stop codon at a predetermined. site.

Having now defined the 3'-terminus of the coding strand or, alternatively, the C-terminus amino acid, the 5'-region or N-terminus of the polypeptide is now defined. Of course, the particular order in which the two termini are modified is primarily one of convenience, and can even be done simultaneously, where primer repair is used at the 5'-end of the coding strand in conjunction with site mutation at the 3'-end.

Different strategies may be evolved, depending upon the nature of the host in which expression is to be obtained, and whether such host recognizes the leader sequence as a secretory signal for secretion of the polypeptide with concomitant removal of the leader sequence polypeptide. Where this opportunity is not available, the strategy will involve removal of the leader sequence to provide a start codon at the 5'-terminus of the sequence of the coding strand coding for the variable region, which sequence can be inserted into an expression vector, so as to be under the control of a predetermined promoter and ribosomal start site.

Based on the sequence of the leader region or the sequence coding for the N-terminus of the variable region, different oligonucleotides for homo- or heteroduplexing can be prepared.

Where the leader sequence is retained, primer repair is employed to remove the 5'-flanking sequence of the coding strand. When the primer repair of the N-terminus is performed simultaneously with the C-terminus mutagenesis, after treatment with the DNA polymerase, the resulting partial double stranded DNA will be treated with a 5'-3'-single strand exonuclease to remove the 5'-flanking region as well as a ligase to provide for covalent linking of the replicated strand to the N-terminus oligonucleotide.

Where the leader sequence is to be removed, in vitro mutagenesis is employed to introduce an f-met codon at. the N-terminus of the DNA sequence coding for the variable region.

Alternative strategies may be employed for recovering the desired ds cDNA and performing the in vitro mutagenesis. If useful restriction sites are distant from the coding regions, the plasmid may be digested with the appropriate restriction endonuclease, followed by digestion with a double-strand exonuclease e.g. Bal 31. The resulting ds cDNA may be cloned and the proper sequence selected and modified, as appropriate, as described above. If the non-coding flanking region at the 5'-terminus of the coding strand is too long, it may be digested with an endonuclease, where a convenient restriction site is available or by digestion with an exonuclease e.g. Bal 31.

By repeating the above described procedure for modifying the 3'-terminus, except that the oligonucleotide is now complementary to the non-coding (nonsense) strand, and includes an initiation codon at the 5'-end (primer repair) or within the oligonucleotide (in vitro mutagenesis), the 5'-terminus of DNA sequence encoding the variable regions may be tailored. Normally, the oligonucleotide homoduplexes for primer repair and heteroduplexes for in vitro mutagenesis. In this way, "tailored" ds-cDNA is obtained which has start and stop codons properly positioned to define the variable regions of both the light and heavy chains of immunoglobulins. The resulting blunt ended ds cDNA may be modified, e.g. by addition of linkers, to provide complementary termini for insertion into an expression vector in proper spacing to the regulatory signals which are ligated to the ds cDNA or are present in the vector.

The ds cDNA is now ready to be used for insertion into a vector for expression. As distinguished from the earlier vectors, which were solely concerned with replication of the ds cDNA, the vector which is employed at this stage requires the presence of the regulatory signals for transcription and translation.

A vector is chosen having an appropriate promoter, as well as other transcriptional regulatory signal sequences, such as an operator, attenuator, or activator. Also, the vector will have been at least partially sequenced, so as to determine the presence of at least one insertion site for introduction of the ds-cDNA coding for the variable regions at a site under the control of the regulatory signals.

Besides transcriptional regulatory signals there are, as already indicated, translational regulatory signals, primarily the ribosomal binding site (Shine-Dalgarno sequence, "S-D") and the initiation codon ("f-met codon"). The S-D sequence and the initiation codon must be in the proper spacing, generally spaced apart by from about 3 to 12 base pairs. The S-D sequence may be present on the vector in appropriate juxtaposition to an insertion site or may be joined to the variable region coding sequence, for example, by ligation of an oligonucleotide providing the S-D sequence and an appropriate restriction site upstream from the S-D sequence. Alternatively, the S-D sequence may be introduced by in vitro mutagenesis, as previously described. The coding sequence must be in frame with the initiation codon.

In choosing the different strategies, considerations include the presence or absence of particular restriction sites in the variable region coding sequence and flanking regions; the availability of vectors which allow for insertion of the ds cDNA sequence into the vector and expression of the variable region polypeptide; the availability of useful shuttle vectors; the availability of hosts which permit expression and isolation in good yield; and the ability of the host to recognize such signals as secretory signals to cleave off the leader sequence. Therefore, in each situation with each different idiotype, it will be necessary to restriction map at least portions of the DNA sequence coding for the variable region and the flanking regions.

Where the termini of the vector and sequence to be inserted are the same, there will be the further concern that the inserted sequence may be in the correct or incorrect orientation. By mapping the resulting cloned plasmids after insertion, one can select for those plasmids having the variable region sequence in the proper orientation.

The above strategy allows for a number of important advantages. The polypeptide chains are prepared as a homogeneous composition containing identical sequences and chain lengths. The polypeptides forming the rFv will be free of sugars. By virtue of the homogeneous and unglycosylated character of the polypeptides, the polypeptides may be more uniformly labeled or modified. In this way products are obtained of uniform and reproducible properties. Thus, the products may be reliably administered to a mammalian host without concern for unexpected responses due to a heterogeneous spectrum of products.

To recapitulate, in order to provide a homogeneous rFv having high binding affinity, the evolutionary immune process is used as the focal point of the hybrid DNA strategy. The following steps are employed. The messenger RNA from a hybridoma cell or other monoclonal antibody-producing cell is isolated and used to prepare a cDNA transcript from the messenger encoding the light and/or heavy chains of the immunoglobulin. Based on the flanking sequences upstream and downstream, at the initiation (may include leader region) and termination of the variable region, short DNA sequences at least partially complementary to those sequences are employed for primer repair or in vitro mutagenesis to remove extraneous flanking regions and to introduce translational control signals. The in vitro mutagenesis employs an oligonucleotide, which heteroduplexes with one of the strands of the cDNA, in combination with Klenow fragment of DNA polymerase I. Primer repair requires a homoduplexing oligonucleotide in combination with the same enzyme. The process is repeated twice to provide ds cDNA coding for the variable region with translational regulatory signals at predetermined sites. This ds cDNA is inserted into an appropriate vector, e.g. plasmid, to provide a DNA expression construct capable of self-replication and having the proper regulatory signals for replication, selection and expression.

The resulting construct is then introduced into an appropriate host to provide expression of the heavy or light polypeptide members of the rFv and the polypeptides isolated. The heavy and light polypeptide members of the rFv are then combined in an appropriate medium to form the rFv.

In view of the fact that the idiotypes vary, the sequence of steps of the subject invention permits the accommodation of a wide variety of coding sequences for variable regions. Also, the ds cDNA and vector can be tailored to optimize the regulatory signals which are employed, particularly the promoter. The ribosome binding site and variable-region initiation codon may be properly spaced to optimize expression of the variable-region polypeptide.

The constructs containing the variable region coding sequence in the proper orientation are used to transform the appropriate host for expression. The resulting transformants are selected by virtue of the markers present in the vector, cloned and expanded. The polypeptide produced by the transformants may be isolated by separation of the cells and isolation of the supernatant into which such polypeptides are secreted. Or, if the polypeptides are not secreted, the transformant cells are isolated and lysed and the polypeptide recovered. Fractions containing enhanced amounts of the variable region polypeptide may be obtained by various conventional techniques, such as gel electrophoresis, fractional precipitation, affinity chromatography, high pressure liquid chromatography, or the like. In any event, the original lysate, or supernatant, or the concentrated fractions therefrom, may be screened for the presence of the variable-region polypeptides by immunoassay.

Where the heavy and/or light chain is secreted, the chains may be isolated as follows. Polyclonal antisera to monoclonal immunoglobulin can be prepared by immunizing an appropriate vertebrate with the whole monoclonal antibody, so as to produce antiserum which recognizes the determinant sites of the heavy and light chains. Antibodies recognizing the whole immunoglobulin or only the light or heavy chain may be substantially separated and purified from other antibodies in the antiserum. By binding to and eluting from affinity columns containing whole immunoglobulin, or only the heavy or light chains, covalently linked to an appropriate support, the antibodies for the whole immunoglobulin, or heavy or light chain respectively, become bound to the column. After denaturing the column and removing the purified antibodies, the antibodies are then conjugated to an appropriate support to provide an affinity column to purify the heavy or light chains of the rFv.

Where the light or heavy chain is not secreted, the transformed microorganisms containing the appropriate ds cDNA for either light or heavy chains are grown in liquid cultures and cleared lysates prepared. These lysates are then passed over an immunosorbent affinity column prepared as described above, employing the specific polyclonal antisera. The bound variable regions are eluted from the column with an appropriate denaturing solvent. The eluates from each of the heavy and light chain isolations are pooled, followed by treatment to renature the polypeptides to form L-rFv and H-rFv respectively. For renaturation, the pooled eluates may be dialyzed against appropriate aqueous buffered solutions. The mixture is then further purified by passing over the appropriate ligand-affinity column and the bound molecules eluted with an appropriate denaturing solvent. The variable regions are then renatured as previously described to provide a solution of rFvs which may then be used for a variety of purposes.

In accordance with the subject invention, molecules are provided which are polypeptide duplexes of the variable region of light and heavy chains of immunoglobulins, retaining the specificity of the immunoglobulins. By lacking the constant regions, the rFvs are less immunogenic and may, therefore, be prepared from sources xenogenic to a host to which they are to be administered. Furthermore, the rFvs are a homogeneous mixture, rather than a heterogeneous mixture. The heterogeneous mixtures will contain chains of varying lengths, which mixtures may be obtained by other techniques, such as enzyme and acid treatment. The homogeneity of the compositions of the subject invention allows for uniform modification and accurate determination of therapeutic levels. In addition, there is no contamination with chains from whole immunoglobulins which were inadequately digested, so as to retain immunogenic portions or uncover new immunogenic sites. Finally, large amounts of the desired rFvs may be prepared in high yield and high purity.

The following examples are also by way of illustration and not by way of limitation.

EXPERIMENTAL

Exemplary of various ligands, the following description will be directed to the dinitrophenyl ligand. It is to be understood that the subject process will be useful for any ligand, although due to the wide variety of idiotypes involved, at various stages the strategies may be required to be modified slightly to accommodate the presence of a particular restriction site or other unique event.

Example 1

Preparation of Monoclonal Antibodies for Dinitrophenyl

Into an aqueous buffered medium at about pH 10.5 is introduced 10 mmoles 2,4-dinitrobenzene. sulfonate and 0.01 mmole of keyhole limpet hemocyanin and the mixture rocked for 20 hours at room temperature. The solution is then dialyzed against successive changes of 0.6M NaCl and the residue isolated to be used for immunization.

The DNP immunogen (100 $\mu$g) is combined as an emulsion with 0.1 ml complete Freund's adjuvant and 0.1 ml PBS. To each of 6 BALB/c mice is injected 0.2 ml of the above formulation. Each mouse receives four injections at weekly intervals. Each dose contains a total of 100 $\mu$g of the immunogen distributed intraperitoneally as well as subcutaneously into foot pads and into inguinal areas. The first injection is given with complete and the remaining with incomplete Freund's adjuvant. Three days after the last injection, the mice are sacrificed, the spleens isolated and used for formation of monoclonal antibodies.

The fusion is performed by combining $3\times10^7$ Sp2/0-Ag14 myeloma cells (Shulman et al. (1978) *Nature* 276:269–270) and $5\times10^7$ spleen cells and the mixture centrifuged at 200 g for 5 min and resuspended slowly in 0.6 ml 50% PEG 1500 in Dulbecco's modified Eagle's medium (Flow). After 1 min at 37° C., 20 ml of R medium (RPMI 1640 medium (Gibco) supplemented with 30 mM Hepes (Flow)) is added slowly. The cells are then centrifuged and resuspended in 20 ml of R medium supplemented with 10% fetal calf's serum (Gibco) (RF medium) and 0.2 ml of this suspension is then distributed to each of 200 wells containing 0.8 ml RF medium. One hundred of these wells also contain $2\times10^5$ mouse peritoneal exudate cells. After 24 h incubation, 1 ml RF supplemented with HAT medium is added to each well. Every 2–3 days, 1 ml of the medium is replaced with fresh RF+HAT. After two weeks, the cells demonstrating growth are tested for immunoglobulin production employing $^{35}$S-2,4-dinitrophenylsulfenamide of lysine. Clones showing specific activity are cloned by plating in soft agar to provide anti-DNP as required.

Alternatively, one may use the method described by Herzenberg et al. (1980) J. Exp. Med. 151: 1071–1087. In this method, DNP substituted bovine serum albumin is added to individual wells in a microtiter plate in an RIA diluent (1% BSA, 0.005M EDTA and 0.1% NaN$_3$ in PBS pH 7.6) (50 $\mu$l, 0.05 mg/ml) and the mixture is incubated for 1 h in the wells. Test or standard antisera at various dilutions are then added to coated wells (20 $\mu$l/well) and incubated for 1 h. After washing three times with the RIA diluent, $^{125}$I-labeled anti-mouse immunoglobulin (approximately $2\times10^5$ cpm/well) is added and the mixture is incubated for 1 h. Plates are then washed 3× with the RIA diluent, dried and evaluated by autoradiography.

Both of these methods of detecting the presence of the desired antibody are well known. The cells are then cloned either by limiting dilution or cloning in soft agar and the resulting cloned cell lines are propagated and stored frozen in liquid nitrogen for use as required.

Cells from one of the positive cloned cell lines are grown to a density of about $1\times10^6$ cells/ml in a 1 L culture. The cells are harvested by centrifugation and 1 gram of the cells is dropped into 16 ml of guanidinium thiocyanate stock solution (4M, 50 g of guanidinium thiocyanate with 0.5 g of sodium N-lauryl sarcosine, 2.5 ml of 1M sodium citrate, pH 7.0, 0.7 ml of 2-mercaptoethanol and 0.5 ml of Sigma 30% Antifoam A, and the volume brought to 100 ml at room temperature) in a 55 ml Potter-Elbehjem homogenizer tube and is immediately homogenized for 30–60s at full speed with an 18 mm diameter Tissumizer homogenizer (Tekmar Industries) The resulting homogenate is centrifuged for 10 min at 8,000 rpm in a Sorval HB4 swinging bucket rotor at 10° C. The supernatants are decanted into a flask, mixed with 0.024 volume (relative to the original volume of homogenizing buffer) of 1M acetic acid to lower the pH from 7 to 5 and 0.75 volume of absolute ethanol. After capping and shaking the flask thoroughly, the flask is stored at −20° C. overnight and the material sedimented by centrifugation for 10 min at −10° C. at 6,000 rpm in an HB4 rotor.

The resulting firm pellet is isolated, resuspended by vigorous shaking in 0.5 volume buffered guanidine hydrochloride stock solution (7.5M, neutralized and then buffered with 0.25 volume of 1M sodium citrate, pH 7.0, 5 mM in dithiothreitol). The samples are briefly warmed in a 68° C. water bath to insure complete dispersion of the pellets, followed by precipitation by adding 0.025 volume (relative to the amount of guanidine hydrochloride) of 1M acetic acid in 0.5 volume ethanol. After maintaining the solution for at least. 3 h at −20° C., the solution is centrifuged and reprecipitated with guanidine hydrochloride as described. The reprecipitated material is centrifuged for 5 min at 6,000 rpm and thereafter all reactions are carried out under sterile conditions.

The final pellets are dispersed in ethanol at room temperature, triturated to extract excess guanidine hydrochloride and then centrifuged for 5 min at 6,000 rpm. The ethanol is evaporated with a stream of nitrogen and the RNA pellets dissolved with vigorous shaking in 1 ml of sterile water per g. of original cells. After centrifugation for 10 min at 13,000 rpm at 10° C., the supernatant containing the RNA is decanted. To insure the complete extraction of all. the RNA, the insoluble material is reextracted twice with 0.5 ml of sterile water, the extract centrifuged for 10 min at. 13,000 rpm at 10° C. and the aqueous solutions combined, mixed with 0.1 volume of 2M potassium acetate, pH 5 and 2 volumes of ethanol and left overnight at −20° C.

The RNA is sedimented from the ethanol suspension by centrifugation for 20 min at 20,000 rpm at −10° C. in Corex tubes in an HB4 rotor. The resulting pellets are thoroughly washed with 95% ethanol, dried with nitrogen and dissolved in 1 ml/g cells of 10 mM Tris buffer pH 7.5, 1 mM EDTA, 0.2% SDS. After dissolution of the RNA pellet, ⅕ volume of 5M NaCl is added, and the solution applied to an oligo(dT) column (about 0.5 g dry weight, T3 grade, Collaborative Research). The column is washed extensively with 0.5M NaCl, 10 mM Tris, 1 mM EDTA, pH 7.5 0.2% SDS, and then eluted with 10 mM Tris, EDTA pH 7.5, 0.05% SDS. The elution profile is monitored at $A_{260}$. The UV absorbing fractions are pooled and precipitated by addition of sodium acetate, pH 5 and 2.5 volumes of ethanol. The dried pellet is dissolved in 50 µl (1 vol.) 10 mM Tris 7.5 1 mM EDTA, and 9 vol. DMSO added, immediately followed by 1 vol. of buffered 1M LiCl (1M LiCl, 50 mM EDTA, 2.0% SDS, 10 mM Tris, pH 6.5). This solution is heated at 55° for 5 min, 100 vol. of binding buffer added, and then reapplied to the oligo(dT) cellulose column, equilibrated with binding (0.5M NaCl, 10 mM Tris, 1 mM EDTA, 0.2% SDS) buffer and eluted as before.

The presence of messenger RNA encoding the monoclonal immunoglobulin heavy and light chain polypeptides is verified by hybrid selection employing DNA clones of the appropriate heavy and light chain genes from sources described in Early and Hood, Genetic Engineering (1981) Vol. 3, Setlow and Hollander, Plenum Publishing Corp., pages 157–188. DNA probes can be prepared by synthesis, based on published amino acid sequences or published DNA sequences or obtained from a variety of sources reported in Early and Hood, supra. The DNA probes are denatured, neutralized and bound to nitrocellulose filter paper (Schleicher and Schuell BA-85-R 597) according to the method of Southern, J. Mol. Biol. (1975) 98:503–517, in 10× conc. standard citrate. (See also, U.S. Pat. No. 4,302, 204.) The probes are hybridized to 30 µg of the messenger RNA in 65% formamide/10 mM Pipes, pH 6.4/0.4M NaCl in a final volume of 100 µl at 50° C. for 2 h. The reaction mixture is spun for 10 sec. in a Microfuge, vortexed, spun again and then gently vortexed to resuspend the filters. The mixture is incubated at 50° C. for about 1 h with mild agitation. The reaction mixture is then removed and the filters are washed in 1 ml 0.15M NaCl/0.015M Na citrate/ 0.5% NaDodSO$_4$ 10×, while maintaining the wash buffer at 60° C. After each addition of wash buffer, the tubes are vortexed for several seconds. The filters are then washed twice with 1 ml 10 mM Tris, pH 7.8, 2 mM EDTA, the tubes being incubated at 60° C. for 5 min and the solution removed by aspiration.

RNA is eluted from the RNA-DNA hybrid by boiling the filters for 60 sec in 300 µl of double distilled, sterile water and then quick-frozen in a methanol/dry ice bath. The liquid is removed and brought to a final concentration of 0.2M of sodium acetate and 20 µg of calf thymus tRNA is added. The RNA is precipitated with 2.5 volume of ethanol at −20° C. and immediately prior to translation the RNA is pelleted at 12,000 g for 10 min at 4° C., the pellet washed twice with 70% ethanol and then dried under reduced pressure.

The eluted mRNA is now translated in vitro with rabbit reticulocyte cell-free extract. A translation kit, such as the commercially available kit from New England Nuclear may be employed. After translation, the presence of protein synthesis is determined in accordance with the instructions of the supplier.

After establishing the presence of translation of messenger RNA, aliquots are taken and incubated with monoclonal antibodies in substantial excess to the amount of expression product in the lysate composition. The complex is then precipitated with S. aureus and the precipitates are washed 3× in 0.05M tris, pH 8.3, 0.45M NaCl in 0.5% NP40, boiled in 0.01M sodium phosphate buffer, pH 7.5, containing 1% β-mercaptoethanol and electrophoresed on 5–20% gradient SDS-polyacrylamide gels. The gels are run at 125 V for 1 h after the bromophenol blue marker runs off the end of the gel. The gels are then dried, fixed and autoradiographed on Kodak X-R film.

Having established the presence of messenger RNA coding for immunoglobulin light and heavy chains, the messenger RNA mixture is then employed to prepare a library of double stranded cDNA employing the method of Okayama and Berg, supra. Four hundred µg of pBR322-SV40 (0.71–0.86) DNA are digested at 37° with 700 units of KpnI endonuclease in a reaction mixture (0.4 ml) containing 5 mM tris-HCl (pH 7.5), 6 mM MgCl$_2$, 6 mM NaCl, 6 mM 2-mercaptoethanol and 0.1 mg/ml bovine serum albumin (BSA). After 5 hrs, the digestion is terminated with 40 µl of 0.25M EDTA (pH 8.0) and 20 µl of 10% SDS; the DNA is recovered following extraction with water saturated phenol-CHCl$_3$(1:1) (hereafter referred to as phenol-CHCl$_3$) and ethanol precipitation.

Homopolymer tails averaging 60, but not more than about 80, dT residues per end are added to the KpnI endonuclease-generated termini with calf thymus terminal deoxynucleotidyl transferase as follows: The reaction mixture (0.2 ml) contains as buffer 140 mM sodium cacodylate-30 mM tris-HCl (pH 6.8), 1 mM CoCl$_2$, 0.1 mM dithiothreitol, 0.25 mM dTTP, the KpnI endonuclease-digested DNA and 400 units of the terminal deoxynucleotidyl transferase. After 30 minutes at 37° C. the reaction is stopped with 20 µof 0.25M EDTA (pH 8.0) and 10 µl of 10% SDS and the DNA is recovered after several extractions with phenol-CHCl$_3$ by ethanol precipitation. The DNA is then digested with 17 units of HpaI endonuclease in 0.2 ml containing 10 mM Tris-HCl (pH 7.4), 10 mM MgCl$_2$, 20 mM KCl, 1 mM dithiothreitol and 0.1 mg/ml BSA for 5hrs at 37° C.

The large DNA fragment, which contains the origin of pBR322 DNA replication and the gene conferring ampicillin resistance, is purified by agarose (1%) gel electrophoresis and is recovered from the gel by a modification of the glass powder method (Vogelstein and Gillespie, PNAS USA (1979) 76:615–619).

The dT-tailed DNA is further purified by adsorption and elution from an oligo dA-cellulose column as follows: The DNA is dissolved in 1 ml of 10 mM tris-HCl (pH 7.3) buffer containing 1 mM EDTA and 1M NaCl, cooled to 0° and applied to an oligo dA-cellulose column (0.6×2.5 cm) equilibrated with the same buffer at 0°. The column is washed with the same buffer at 0° and eluted with water at room temperature. The eluted DNA (140 µg) is precipitated with ethanol and dissolved in 100 µl of 10 mM Tris-HCl (pH 7.3) with 1 mM EDTA.

The oligo dG-tailed linker DNA is prepared by digesting 100 µg of pBR322-SV40 (0.19–0.32) with 120 units of PstI endonuclease in 0.2 ml containing 6 mM Tris-HCl (pH 7.4), 6 mM MgCl 6 mM 2-mercaptoethanol, 50 mM NaCl and 0.1 mg/ml BSA. After 1.5 hrs at 37° the reaction mixture is extracted with phenol-CHCl$_3$ and the DNA is precipitated with alcohol. Then, tails of 10–15 dG residues are added per end with 60 units of terminal deoxynucleotidyl transferase in the same reaction mixture (50 μl) described above, except for 0.1 mM dGTP replacing dTTP. After 20 minutes at 37° C. the mixture is extracted with phenol-CHCl$_3$ and after the DNA is precipitated with ethanol it is digested with 50 units of HindIII endonuclease in 50 μl containing 20 mM Tris-HCl (pH 7.4), 7 mM MgCl$_2$, 60 mM NaCl and 0.1 mg/ml BSA at 37° for 1 hr. The small oligo dG-tailed linker DNA is purified by agarose (1.8%) electrophoresis and recovered as described above.

The reaction mixture (10 μl) contains 50 mM Tris-HCl (pH 8.3), 8 mM MgCl$_2$, 30 mM KCl, 0.3 mM dithiothreitol, 2 mM each dATP, dTTP, dGTP, and $^{32}$P-dCTP (850 cpm/pmol), 0.2 μg of the mrRNA (about 2–3 fold excess over primer ends), 1.4 μg of the vector-primer DNA (0.7 pmole primer end) and 5 units of reverse transcriptase. (The molar ratio of polyA mRNA to vector-primer DNA ranges from about 1.5–3).

cDNA synthesis is initiated by the addition of reverse transcriptase and continued at 37° for 20 min. By this time the rate of dCTP incorporation levels off and more than 60% of the primer is utilized for cDNA synthesis. The reaction is stopped with 1 μl of 0.25M EDTA (pH 8.0) and 0.5 μl of 10% SDS; 10 μl of phenol-CHCl$_3$ is added and the solution vortexed vigorously and then centrifuged. After adding 10 μl of 4M ammonium acetate and 40 μl of ethanol to the aqueous phase, the solution is chilled with dry ice for 15 min, warmed to room temperature with gentle shaking to dissolve unreacted deoxynucleoside triphosphates that precipitate during chilling, and centrifuged for 10 min in an Eppendorf microfuge. The pellet is dissolved in 10 μl of 10 mM Tris-HCl (pH 7.3) and 1 mM EDTA, mixed with 10 μl of 4M ammonium acetate and reprecipitated with 40 μl of ethanol, and then rinsed with ethanol.

The pellet containing the cDNA:mRNA-plasmid is dissolved in 15 μl of 140 mM sodium cacodylate-30 mM Tris-HCl (pH 6.8) buffer containing 1 mM CoCl$_2$, 0.1 mM dithiothreitol, 0.2 μg of poly A, 66 μM $^{32}$P-dCTP (6000 cpm/pmol) and 18 units of terminal deoxynucleotidyl transferase. The reaction is carried out at 37° for 5 min to permit the addition of 10 to 15 residues of dCMP per end and then terminated with 1.5 μl of 0.25M EDTA (pH 8.0) and 0.75 μl of 10% SDS. After extraction with 15 μl of phenol-CHCl$_3$ the aqueous phase is mixed with 15 μl of 4M ammonium acetate and the DNA is precipitated and reprecipitated with 60 μl of ethanol and the final pellet rinsed with ethanol.

The pellet is dissolved in 10 μl of buffer containing 20 mM Tris-HCl (pH 7.4), 7 mM MgCl$_2$, 60 mM NaCl and 0.1 mg/ml BSA and then digested with 2.5 units of HindIII endonuclease for 1 hr at 370°. The reaction is terminated with lμl of 0.25M EDTA (pH 8.0) and 0.5 μl of 10% SDS and, after extraction with phenol-CHCl$_3$, followed by the addition of 10 μl of 4M ammonium acetate, the DNA is precipitated with 40 μl of ethanol. The pellet is rinsed with ethanol, dissolved in 10 μl of 10 mM Tris-HCl (pH 7.3) and 1 mM 3 μl of ethanol are added to prevent freezing during storage at −20° C.

One μl of the HindIII endonuclease-digested oligo dC-tailed cDNA:mRNA-plasmid (0.02 pmol) is incubated in a mixture (10 μl) containing 10 mM Tris-HCl (pH 7.5) 1 mM EDTA, 0.1M NaCl and 0.04 pmol of the oligo dG-tailed linker DNA (this amount is a two-fold molar excess over the quantity of the vector-cDNA:mRNA and of the fragment which remains as a result of the HindIII endonuclease digestion in the previous step) at 65° for 2 min., followed by 42° for 30 min. and then cooled at 0°. The mixture (10 μl) is adjusted to a volume of 100 μl containing 20 mM Tris-HCl (pH 7.5), 4 mM MgCl$_2$, 10 mM (NH$_4$)$_2$SO$_4$, 0.1M KCl, 50 μg/ml BSA and 0.1 mM β-NAD; after adding 0.6 μg of *E. coli* DNA ligase the solution is incubated overnight at 12°.

To replace the RNA strand of the insert, the ligation mixture is adjusted to contain 40 μM of each of the four deoxynucleotide triphosphates, 0.15 mM β-NAD, 0.4 μg of additional *E. coli* DNA ligase, 0.3 μg of *E. coli* DNA polymerase I, and 1 unit of *E. coli* RNase H. This mixture (104 μl) is incubated successively at 12° and room temperature for 1 hr each to promote optimal repair synthesis and nick translation by PolI. The reaction is terminated by the addition of 0.9 ml of cold 10 mM Tris-HCl (pH 7.3) and 0.1 ml aliquots are stored at 0°.

Transformation is carried out using minor modifications of the procedure described by Cohen et al., PNAS USA (1972) 69:2110–2114. *E. coli* K12 (strain HB101) is grown to 0.5 A$_{600}$ at 37° C. in 20 ml L-broth. The cells are collected by centrifugation, suspended in 10 ml of 10 mM Tris-HCl (pH 7.3) containing 50 mM CaCl$_2$ and centrifuged at 0° for 5 min. The cells are resuspended in 2 ml of the above buffer, incubated again at 0° for 5 min.; then, 0.2 ml of the cell suspensions is mixed with 0.1 ml of the DNA solution and incubated at 0° for 15 min. After the cells are kept at 37° for 2 min. and at room temperature for 10 min., 0.5 ml of L-broth is added, the culture incubated at 37° for 30 min, and then plated on nitrocellulose filters on agar plates containing 50 μg/ml ampicillin. After incubation at 37° for 12–24 hrs. *E. coli* transformants are screened for the presence of the light and heavy chain cDNA according to the method of Grunstein and Hogness by in situ colony hybridization. Several thousand transformants are grown on three replica nitrocellulose filter discs, lysed with alkali and hybridized with the probes described previously for the constant regions of the heavy and light immunoglobulin chains. Clones of the genes coding for the heavy and light immunoglobulin chains are identified. Colonies that give positive hybridization signals are grown in one-liter of L-broth containing 50 μg/ml of ampicillin and their plasmid DNAs are isolated by standard techniques (Gunsalus et al., J. Bact. (1979) 140:106–113).

The cells are lysed as described previously, the lysate cleared by centrifugation and the cleared lysate diluted with an equal volume of water. RNase A is added to 50 μg/ml and after 1 h at 37° C., the lysate is extracted with 0.3 volume of phenol saturated with TE buffer (10 mM tris-HCl, pH 7.9, plus 1 mM EDTA). After centrifugation (16,000×g, 4° C., 10 min), the aqueous phase is removed, adjusted to 1M NaCl and the DNA precipitated with 2 volumes of ethanol. After several hours at −20° C., the DNA is pelleted by centrifugation (10,000×g, 4° C., 20 min), dried and dissolved in TE buffer.

Each of the cDNA clones are then restriction mapped and sequence analyzed by conventional techniques, so that a restriction map is obtained which allows for subsequent manipulation of the cDNA coding for the variable regions for cloning and expression. The methods of Maxam and Gilbert, Methods Enzymol. (1980) 65:499–560 and Sanger et al., J. Mol. Biol. (1980) 143:161–178 are used, respectively. Those cDNA clones for light chains and heavy chains; encoding the complete variable region and leader sequences are selected for subsequent manipulation.

Illustrative of the subject method will be the isolation, sequencing and manipulation of the κ-chain (light chain) of MOPC41 and the heavy chain of the myeloma S107.

The following is the sequence of the κ-chain of MOPC41, where the sequences encoding the leader, variable region and constant region are separated by gaps, with only the first sixteen amino acids of the constant region indicated. (Seidman et al.,"Nature" (1979) 280: 370–375)

```
                  Met Asp Met Arg Ala Pro Ala
... TCA GGA CTC AGC ATG GAC ATG AGG GCT CCT GCA

Gln Ile Phe Gly Phe Leu Leu Leu Leu Phe Gln Gly
CAG ATT TTT GGC TTC TTG TTG CTC TTG TTT CAA GGT

Thr Arg Cys     Asp Ile Gln Met Thr Gln Ser Pro
ACC AGA TGT ... GAC ATC CAG ATG ACC CAG TCT CCA

Ser Ser Leu Ser Ala Ser Leu Gly Glu Arg Val Ser
TCC TCC TTA TCT GCC TCT CTG GGA GAA AGA GTC AGT

Leu Thr Cys Arg Ala Ser Gln Asp Ile Gly Ser Ser
CTC ACT TGT CGG CCA AGT CAG GAC ATT GGT AGT AGC

Leu Asn Trp Leu Gln Gln Glu Pro Asp Gly Thr Ile
TTA AAC TGG CTT CAG CAG GAA CCA GAT GGA ACT ATT

Lys Arg Leu Ile Tyr Ala Thr Ser Ser Leu Asp Ser
AAA CGC CTG ATC TAC GCC ACA TCC AGT TTA GAT TCT

Gly Val Pro Lys Arg Phe Ser Gly Ser Arg Ser Gly
GGT GTC CCC AAA AGG TTC AGT GGC AGT AGG TCT GGG

Ser Asp Tyr Ser Leu Thr Ile Ser Ser Leu Glu Ser
TCA GAT TAT TCT CTC ACC ATC AGC AGC CTT GAG TCT

Glu Asp Phe Val Asp Tyr Tyr Cys Leu Gln Tyr Ala
GAA GAT TTT GTA GAC TAT TAC TGT CTA CAA TAT GCT

Ser Ser Pro Trp Thr Phe Gly Gly Gly Thr Lys Leu
AGT TCT CCG TGG ACG TTC GGT GGA GGC ACC AAG CTG

Glu Ile Lys Arg     Ala Asp Ala Ala Pro Thr Val
GAA ATC AAA CGT ... GCT GAT GCT GCA CCA ACT GTA

Ser Ile Phe Pro Pro Ser Ser Glu Gln
TCC ATC TTC CCA CCA TCC AGT GAG CAG ...
```

The following is the nucleotide sequence of the heavy chain variable region of myeloma S107, with the leader, variable region and constant region separated by gaps, and only the first nine amino acids of the constant region depicted. (Early et al. (1980), Cell. 19:981–992).

```
Met Lys Leu Trp Leu Asn Trp Val Phe Leu Leu Thr Leu
ATG AAG TTG TGG TTA AAC TGG GTT TTT CTT TTA ACA CTT

Leu His Gly Ile Gln Cys     Glu Val Lys Leu Val Glu
TTA CAT GGT ATC CAG TGT ... GAG GTG AAG CTG GTG GAA

Ser Gly Gly Gly Leu Val Gln Pro Gly Gly Ser Leu Arg
TCT GGA GGA GGC TTG GTA CAG CCT GGG GGT TCT CTG AGA

Leu Ser Cys Ala Thr Ser Gly Phe Thr Phe Ser Asp Phe
CTC TCC TGT GCA ACT TCT GGG TTC ACC TTC AGT GAT TTC

Tyr Met Glu Trp Val Arg Gln Pro Pro Gly Lys Arg Leu
TAC ATG GAG TGG GTC CGC CAG CCT CCA GGG AAG AGA CTG

Glu Trp Ile Ala Ala Ser Arg Asn Lys Ala Asn Asp Tyr
GAG TGG ATT GCT GCA AGT AGA AAC AAA GCT AAT GAT TAT

Thr Thr Glu Tyr Ser Ala Ser Val Lys Gly Arg Phe Ile
ACA ACA GAG TAC AGT GCA TCT GTG AAG GGT CGG TTC ATC

Val Ser Arg Asp Thr Ser Gln Ser Ile Leu Tyr Leu Gln
GTC TCC AGA GAC ACT TCC CAA AGC ATC CTC TAC CTT CAG

Met Asn Ala Leu Arg Ala Glu Asp Thr Ala Ile Tyr Tyr
ATG AAT GCC CTG AGA GCT GAG GAC ACT GCC ATT TAT TAC

Cys Ala Arg Asp Tyr Tyr Gly Ser Ser Tyr Trp Tyr Phe
TGT GCA AGA GAT TAC TAC GGT AGT AGC TAC TGG TAC TTC

Asp Val Trp Gly Ala Gly Thr Thr Val Thr Val Ser Ser
GAT GTC TGG GGC GCA GGG ACC ACG GTC ACC GTC TCC TCA

Ala Lys Thr Thr Pro Pro Thr Val Tyr
... GCC AAA ACG ACA CCC CCA TCT GTC TAT ...
```

Based on the DNA sequencing and the restriction map, PstI sites are found at the −110 base pair of the coding strand and downstream from the termination site for the cDNA coding for the light chain, while convenient Hind III restriction sites are found upstream from the leader sequence and downstream from the termination site of the coding strand for the heavy chain. The leader sequences and coding sequences of the light and heavy chain variable regions are free of sequences recognized by the indicated endonucleases.

The isolated plasmid DNAs are digested with the respective endonucleases in accordance with the instructions of the supplier and the resulting fragments purified by electrophoresis on agarose gels (Seakem). The gels are 2% agarose, 15 cm×15 cm×0.2 cm and 100 V for 2 h is applied. By employing markers, the band of the appropriate molecular weight is located and excised. The gel slice is placed directly into an 1.5 ml Eppendorf tube, rapidly frozen and thawed twice in a Dry Ice-alcohol bath and then centrifuged 5 min in the Eppendorf centrifuge (15,000 rpm) and the supernatant recovered. The supernatant is boiled in 6×SSC to denature the DNA and provide single strands, followed by cooling to 0° C.

Based on the DNA sequence, a DNA oligomer is prepared which is at least partially complementary to a short sequence of each of the non-coding ("anti-sense") strands of the variable region sequences of the light and heavy chains. The oligomer has an f-met codon at its 5'-end and is complementary to the downstream nucleotides at the N-terminus of the leader sequence for primer repair: or has an f-met codon intermediate its ends and complementary sequences to the 3'-end of the coding sequence for the leader region and the 5'-end of the coding sequence for the variable regions for in vitro mutagenesis. The oligomers are readily prepared in accordance with the methods described by Itakura et al. J. Biol. Chem. (1975) 150:4592.

The following schemes depict the primer repair synthesis method for the light and heavy chains where the leader sequence is retained (a and b, respectively) and the in vitro mutagenesis method where the leader sequence is removed and an f-met codon introduced at the N-terminus of the coding sequence for the variable regions of the light and heavy chains (c and d, respectively).

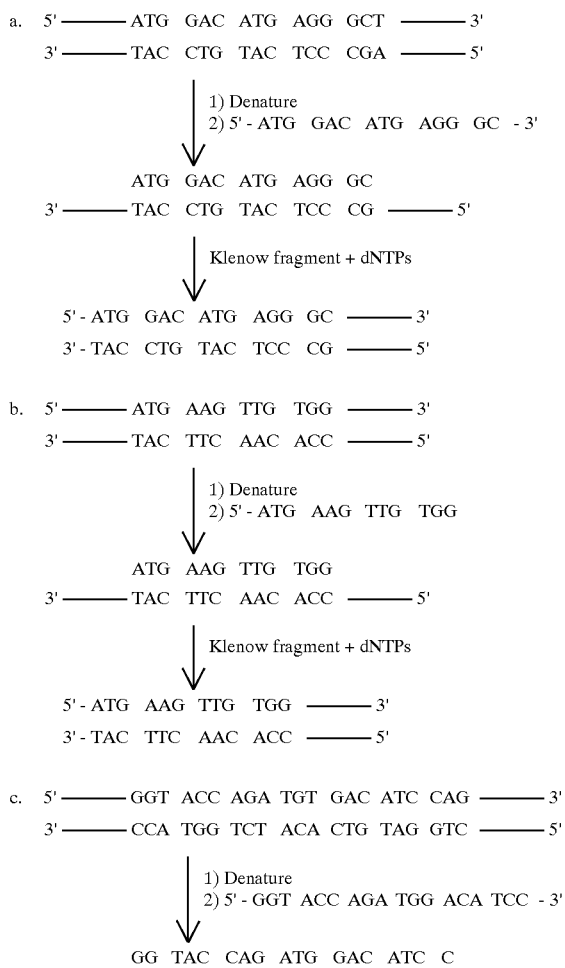

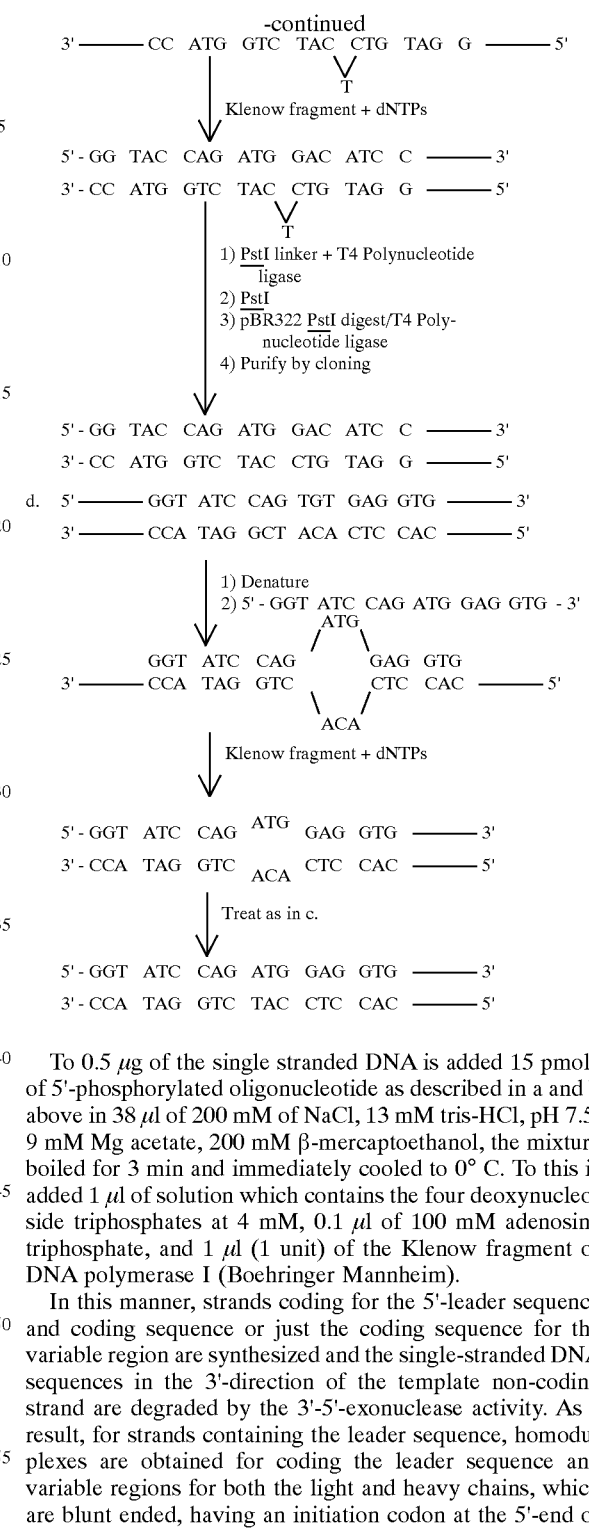

To 0.5 μg of the single stranded DNA is added 15 pmole of 5'-phosphorylated oligonucleotide as described in a and b above in 38 μl of 200 mM of NaCl, 13 mM tris-HCl, pH 7.5, 9 mM Mg acetate, 200 mM β-mercaptoethanol, the mixture boiled for 3 min and immediately cooled to 0° C. To this is added 1 μl of solution which contains the four deoxynucleoside triphosphates at 4 mM, 0.1 μl of 100 mM adenosine triphosphate, and 1 μl (1 unit) of the Klenow fragment of DNA polymerase I (Boehringer Mannheim).

In this manner, strands coding for the 5'-leader sequence and coding sequence or just the coding sequence for the variable region are synthesized and the single-stranded DNA sequences in the 3'-direction of the template non-coding strand are degraded by the 3'-5'-exonuclease activity. As a result, for strands containing the leader sequence, homoduplexes are obtained for coding the leader sequence and variable regions for both the light and heavy chains, which are blunt ended, having an initiation codon at the 5'-end of the coding strand with the remaining DNA sequence in frame with the initiation codon.

To the resulting blunt ended duplex coding for the leader sequence and variable region of the chains, restriction enzyme linkers are ligated through the use of appropriate phosphorylated linkers, for example, PstI linkers, employing T4 polynucleotide ligase under conditions specified by the supplier. The vector pBR322 is cleaved with PstI to provide cohesive ends for linking to the modified cDNA.

Each of the cDNAs are combined with the linear pBR322 having complementary termini. Equal molar amounts of the vector and cDNAs are combined in an annealing buffer essentially as described in Steinmetz et al. (1981) Cell. 24:125–134, and the annealed DNA used directly for transformation.

One ml of an overnight bacterial culture $E.$ $coli$ strain HB101 (Boyer and Roulland-Dussiox (1969) J. Mol. Biol. 41:459–472) is grown to $2\times10^8$ cells/ml in L broth, pelleted by centrifugation (Sorval SS34 rotor, 85,000 rpm, 4° C., 5 min) and washed in 0.5 volume cold 10 mM $CaCl_2$. The cell pellet is resuspended in 0.5 volume cold 30 mM $CaCl_2$. After 20-min on ice, the cells are again pelleted and resuspended in 0.1 volume cold 30 mM $CaCl_2$. Then 0.20 ml of the suspension is added to 0.1 ml 30 mM $CaCl_2$ containing the annealed plasmids and incubated on ice for 16 min. Each transformation is then heated to 42° C. for 75 sec prior to the addition of 5 ml L broth.

Transformed cultures are incubated at 37° C. for 2hr. The transformants are then grown in agar plates containing M-9 minimal medium and 10 μg/ml tetracycline. Clones which grow on this medium are then transferred to agar plates having M-9 minimal medium and 40 μg/ml of ampicillin. Those cells which are sensitive to ampicillin and resistant to tetracycline are then screened for the presence of plasmids having the desired cDNA.

The selected clones are then grown in 2 ml of nutrient culture for 18 h. A 0.5 ml aliquot is transferred to a 1.5 ml Eppendorf tube for plasmid extraction. Manipulations are carried out at room temperature unless otherwise indicated. The tube is centrifuged for 15 sec, the supernatant carefully removed with a fine-tip aspirator and the cell pellet is thoroughly suspended in 100 μl of a lysozyme solution containing 2 mg/ml lysozyme 50 mM glucose, 10 mM EDTA, 25 mM tris-HCl (pH 8.0).

After a 30 min incubation at 0° C., 200 μl of alkaline SDS solution (0.2N NaOH, 1% sodium dodecylsulfate) is added and the tube is gently vortexed. The tube is maintained for 5 min at 0° C. and then 150 μl of 3M sodium acetate (pH 4.8) is added. After gently mixing by inversion for a few seconds, a clot of DNA forms and the tube is maintained at 0° C. for 16 min. After centrifugation for 5 min, 0.4 ml of the supernatant is removed, transferred to a second centrifuge tube, 1 ml cold ethanol added and the tube held at −20° C. for 30 min. The precipitate is collected by centrifugation for 2 min and the supernatant removed by aspiration. The pellet is resuspended in 100 μl 0.1M sodium acetate, 200 μl ethanol added, and after 10min at −20° C., the precipitate is again collected by centrifugation, and the pellet is dissolved in 50 μl water.

Substantially, the same procedure as described above is used for in vitro mutagenesis. With the primer repair synthesis, only one homoduplex is formed; with in vitro mutagenesis, a heteroduplex is initially formed which upon transformation and cloning results in two homoduplexes: the original gene sequence; and the modified or "tailored" gene sequence, which includes the change in sequence encoded in the oligomer.

As depicted in c and d, oligomers are prepared which introduce an initiation (f-met) codon at the N-terminus of the coding sequence for the variable regions.

The resulting plasmid DNA is isolated as described above and used again as described above for transformation. However, the resulting transformants are grown in small (2 ml) culture for plasmid isolation. The plasmid DNA prepared from single transformant colonies arising from the second cycle of cloning are assayed by filter blot hybridization on nitrocellulose filters (Wallace et al. (1979) Nucleic Acids Research 6:3543–3556) probing with $^{32}$P-radiolabeled oligomers employed for the mutagenesis so as to insure the isolation of the desired tailored homoduplexes of the cDNA. The clones having the tailored sequence are isolated and the plasmid DNA extracted for further processing at the 3'-end of the coding strand.

The cDNA coding for the variable regions can be excised by digestion with PstI. Repeating the technique described in the previous in vitro mutagenesis, where an ATG ("start") codon is introduced before the codon of the N-terminal amino acid of the mature polypeptide, "stop" codons are introduced at the C-terminus of the variable regions. Oligonucleotides are prepared as described previously having complementary sequences to the coding ("sense") strand of the variable-region cDNA.

The oligonucleotides and the schemes for inserting the stop codon at the end of the variable regions are depicted as follows. The introduction of the stop codon in the κ light chain is set forth in e, while the introduction of the stop codon in the heavy chain is set forth in f.

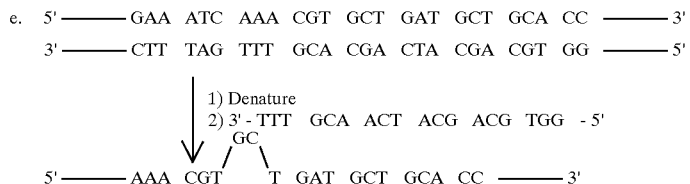

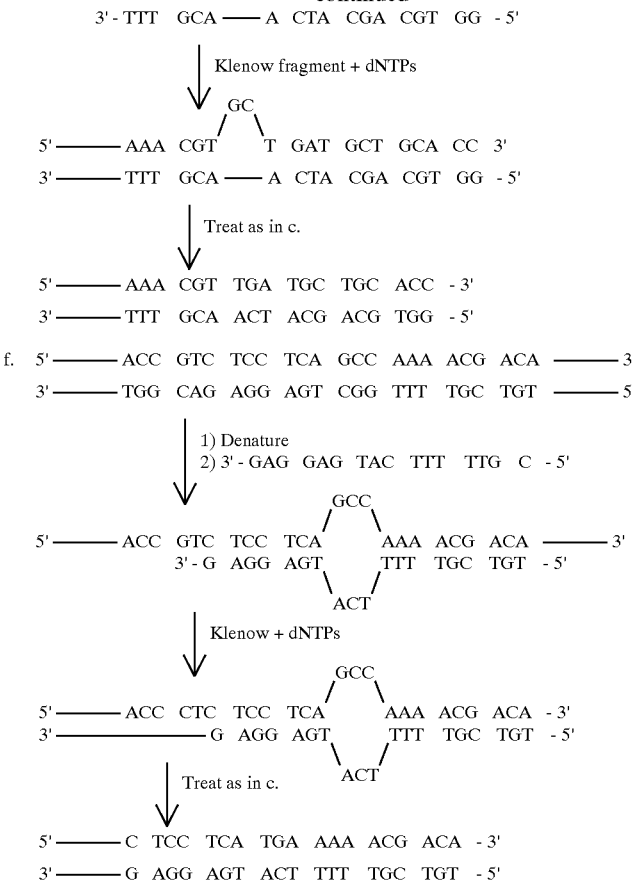

With the replication of the coding strand extending the oligomer having the stop codon, there is also exonuclease activity of the polymerase which degrades the coding strand, removing all of the sequence coding for the constant region, except for the few nucleotides present in the oligonucleotide.

The heteroduplexes having the "tailored" sequences of the variable regions of the light and heavy chains are then ligated to PstI linkers, restricted with PstI endonuclease and inserted into the PstI site of pBR322. After cloning and recloning, the plasmids containing the tailored ds cDNA with the stop codons at the end of the variable regions are isolated and the sequences coding for the variable regions (which may also include the leader sequences) are excised from the pBR322 plasmid using the PstI restriction endonuclease and may now be used for expression of the polypeptide chains of the rFv.

In order to obtain expression of the variable regions, the plasmid pGM1 (pVH253ΔtrpLE1413; Miozarri and Yanofsky, J. of Bacteriol. (1978) 133:1457–1466) is employed. The plasmid is modified to introduce a PstI site which provides for insertion of the sequences coding for the variable regions with the f-met codon in proper position to the Shine-Dalgarno sequence. The following oligonucleotide sequence is prepared:

AGCTGCAGCTTTCGTT.

pGM1(10 μg) is nicked in one strand by digestion with EcoRI (Boehringer Mannheim, 1000 units) in 1 ml of 100 mM tris-HCl, pH 7.2, 50 mM NaCl, 5 mM Mg acetate, 0.01 percent NP-40 and 150 μg/ml ethidium bromide at 37° C. for 1 h. After bringing the reaction mixture to 10 mM EDTA, it is extracted 3×10 volumes water-saturated isobutanol, 1× phenol-CHCl$_3$, 2× ether and 1× isobutanol to reduce the volume to 0.1 ml. After desalting by centrifugation through a 0.5 ml Sephadex G-25 column, the DNA is recovered by precipitation with ethanol. Approximately 5 μg of the nicked DNA is incubated with 40 units of exonuclease III (BRL) in 20 μl of 10 mM tris-HCl, pH 7.5, 2 mM MgCl$_2$ and 1 mM β-mercaptoethanol for 90 min at 37° C. The reaction is adjusted to 15 mM tris-HCl, pH 7.5, 7 mM NaCl, 7 mM MgCl$_2$, 7 mM dithiothreitol. After adding 20 units of bacterial alkaline phosphatase (BRL) and 5 units of HinfI (BRL), digestion is continued for 30 min at 37° C. The mixture is brought to 10 mM EDTA, extracted 233 phenol-CHCl$_3$, 1× ether and desalted by centrifugation through 0.5 ml Sephadex G-25 equilibrated with water.

A major portion of the resulting circular ssDNA is combined with 50 pmole of the 5'-phosphorylated oligonucleotide, depicted above for introducing the PstI site, in 38 μl of 200 mM NaCl, 13 mM tris-HCl, pH 7.5, 9 mM magnesium acetate, 20 mM β-mercaptoethanol, boiled for 30 min and immediately cooled to 0° C. After adding 5 μl of a solution 4 mM in the four dXTP, 0.5p1 of 100 mM ATP, 3p1 (3 units) of DNA polymerase I (Klenow fragment) and 4 μl (10 units) of T4 DNA ligase, the mixture is incubated overnight at 12° C. and then used directly for transformation of E. coli HB101 and the transformants grown, isolated and analyzed using blot hybridization employing radiolabeled $^{32}$P-oligomer to detect clones having the tailored sequence containing the new PstI site.

The "tailored" pGM1 is isolated, partially restricted with PstI and the DNA sequences coding for the light and heavy chain variable regions prepared above inserted individually into the tailored site to provide two plasmids having DNA sequences coding for the light (pGM1L) and heavy (pGM1H) chains, in accordance with the procedure described previously for insertion. The resulting plasmids are used to transform E. coli HB101 and clones having the light and heavy variable region sequences in the desired orientation identified by restriction mapping and purified.

Antisera recognizing the light and heavy chains respectively are produced by using the particular chains as immunogens and the antisera isolated and covalently linked to Sepharose by conventional procedures (March et al., Anal. Biochem. (1974) 60:149–152) and the products employed for affinity columns.

The transformants are grown to cell densities of about $10^9$ cells/ml and collected by centrifugation. The pellet is resuspended in 50 µl of 50 mM tris-HCl, pH 8, 50 mM EDTA, 15% sucrose, 1 mg/ml lysozyme, 0.5% NP40. After 30 min at 0° C., 10 µl of 150 mM tris-HCl, pH 7.5, 280 mM $MgCl_2$, 4 mM $CaCl_2$ and 1 µg DNase are added, followed by centrifugation for 15 min at 12,000 g.

The protein is then isolated by removal of the supernatant from the pellet and the supernatants are passed over the immunosorbent columns (0.15 ml) equilibrated with tris-HCl, pH 7.5. The light and heavy chains of the rFv are eluted with 1M acetic acid, pH 2.5 and the eluates pooled and neutralized with 0.1M NaOH at 0° C. to pH 5.5. The pooled eluates are dialyzed against 3×100 volumes of sodium acetate buffer, pH 5.5, followed by 3×100 volumes PBS, pH 7.

The renatured light and heavy chains of the rFv are further purified by combining the eluates containing the rFv components and passing them over a DNP-affinity column. (In the present example, different sources of heavy and light chains are described, so that this step is done where the source of the two chains is the same.) A DNP-affinity column and procedure is described in Kooistra and Richards, Biochem. (1978) 17:345–351. In addition, sulfhydryl groups may be capped with iodoacetamide as described by Kooistra and Richards, ibid.

The bound rFv is isolated by elution with 1M acetic acid, followed by renaturing with sequential dialysis as described above.

The subject method provides protein complexes of homogeneous composition having two peptide chains which form a complex having high binding affinity for a predetermined haptenic site. The two chains form an rFv having specificity for a particular ligand, by mimicking a naturally occurring immunoglobulin. By removing the constant regions, the resulting rFv has reduced immunogenicity and lacks peptide sequences which may have undesirable functions for particular applications e.g. complement fixation.

The rFv can be used for a variety of purposes in diagnosis and therapy. Because of the homogeneous nature of the composition, the composition has a fixed reproducible level of immunogenicity. Also, due to the reduced molecular weight, relatively short residence times will be involved after injection into a mammalian host. This is particularly important where the rFv is labeled for diagnosis or therapy employing hazardous labels, such as radionuclides, heavy metals, cytotoxic agents, and the like. Short residence times can also be important where the rFv is used to inhibit physiologically active materials in vivo e.g. hormones, enzymes, surface receptors, lymphocytes or other cells, and the like.

The uniform composition allows for controlled labeling, enhancing the ability to a conjugate label to a particular site on one or the other or both of the chains. The uniformity permits controlled conjugations, accurate determinations of therapeutic activity, easy monitoring of therapeutic effect, enhanced reproducibility of result and control and ease of monitoring of side effects.

The subject method provides for accurate synthesis of polypeptide chains which can be brought together to form a binding site for a predetermined epitopic site. The light and heavy chains prepared by the subject method can be brought together to bind to a particular ligand and may be brought together in the presence or absence of the ligand. Also, the method permits introducing a particular amino acid at either terminus for particular applications e.g. tyrosine for radioiodination. By using monoclonal hybridomas as the source of the DNA for coding the variable regions, the naturally occurring binding efficiency is retained and binding affinity can be widely varied.

Although the foregoing invention has been described in some detail by way of illustration and example for purposes of clarity of understanding, it will be obvious that certain changes and modifications may be practiced within the scope of the appended claims.

What is claimed is:

1. A process of synthesizing a single-chain antibody fragment comprising:

cloning DNA encoding a fragment of an antibody chain comprising 95–125 amino acids of a variable region without a constant region from a hybridoma producing an antibody to a predetermined ligand; and expressing the cloned DNA in a host cell to produce the fragment.

2. The process of claim 1, wherein the antibody chain is a heavy chain.

3. The process of claim 1, wherein the antibody chain is a light chain.

* * * * *